(12) United States Patent
Ling et al.

(10) Patent No.: US 6,200,970 B1
(45) Date of Patent: Mar. 13, 2001

(54) 2,3-BENZODIAZEPINE DERIVATIVES AND THEIR USE AS AMPA-RECEPTOR INHIBITORS

(75) Inventors: István Ling; Gizella Ábrahám; Sándor Sólyom; Tamás Hámori; István Tarnawa; Pál Berzsenyi; Ferenc Andrási; Emese Csuzdi; Márta Szöllősy; Antal Simay; István Lagi; Katalin Horváth, all of Budapest (HU)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/125,008

(22) PCT Filed: Jan. 29, 1997

(86) PCT No.: PCT/DE97/00225

§ 371 Date: Nov. 5, 1998

§ 102(e) Date: Nov. 5, 1998

(87) PCT Pub. No.: WO97/28135

PCT Pub. Date: Aug. 7, 1997

(30) Foreign Application Priority Data

Feb. 1, 1996 (DE) .............................. 196 04 920

(51) Int. Cl.$^7$ ....................... A61K 31/551; C07D 243/02
(52) U.S. Cl. ............................. 514/221; 540/267
(58) Field of Search ............................. 514/221; 540/567

(56) References Cited

U.S. PATENT DOCUMENTS

| 4,322,346 | 3/1982 | Korosi et al. .......................... 260/239 |
| 4,423,044 | 12/1983 | Korosi et al. .......................... 424/244 |
| 4,614,740 | 9/1986 | Lang et al. ............................ 514/221 |
| 5,288,863 | 2/1994 | Somogyi et al. ....................... 540/567 |
| 5,891,871 | * 4/1999 | Xia et al. .............................. 514/219 |

FOREIGN PATENT DOCUMENTS

| 512419 | 11/1992 | (EP) . |
| 2034706 | 6/1980 | (GB) . |
| 2162184 | 1/1986 | (GB) . |

OTHER PUBLICATIONS

DeSarro et al.; "GYKI 52466 and Related 2,3–benzodiazepines as Anticonvulsant Agents in DBA/2 Mice," *European Journal of Pharmacology*, 294, pp. 411–422 (1995).

* cited by examiner

Primary Examiner—Richard L. Raymond
(74) Attorney, Agent, or Firm—Millen, White, Zelano & Branigan, P.C.

(57) ABSTRACT

A compound of formula I

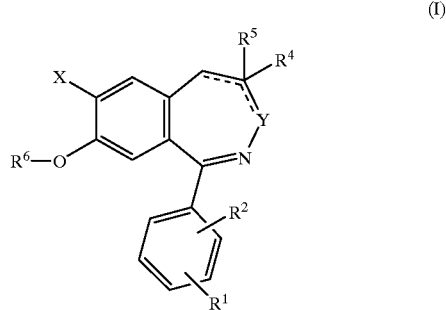

(I)

in which

X means hydrogen or halogen,

Y means $-NR^3-$ or $-N=$, $R^1$ and $R^2$ are the same or different and mean hydrogen, $C_1-C_6$ alkyl, nitro, halogen, the group $-NR^8R^9$, $-O-C_{1-4}$ alkyl, $-CF_3$, OH or $C_{1-6}$ alkanoyloxy, $R^3$ means hydrogen, the group $-CO-R^{10}$, $C_{1-6}$ alkyl or $C_{3-7}$ cycloalkyl, $R^4$ means optionally substituted $C_1-C_6$ alkyl, $R^5$ means hydrogen or $R^4$ and $R^5$ together mean oxygen, $R^6$ means $C_{1-4}$ alkyl, $R^8$ and $R^9$ are the same or different and mean hydrogen, $C_1-C_6$ alkyl or $-CO-C_{1-6}$ alkyl, $R^{10}$ means hydrogen, optionally substituted $C_1-C_6$ alkyl, optionally substituted $C_{6-10}$ aryl, the group $-NR^{11}R^{12}$, $-O-C_{1-6}$ alkyl, $C_{3-7}$ cycloalkyl, $C_{2-6}$ alkenyl or $-O-C_{3-7}$ cycloalkyl, $R^{11}$ and $R^{12}$ are the same or different and mean hydrogen, optionally substituted $C_1-C_6$ alkyl or optionally substituted $C_{6-10}$ aryl and $-C\,\underline{\ldots}\,C\underline{\ldots}$ means a double bond or single bonds or an isomer or physiologically compatible salt thereof with the proviso that the compound is not 1-(3-chlorophenyl)-4-methyl-8-methoxy, 5H-2,3-benzodiazepine.

19 Claims, No Drawings

2,3-BENZODIAZEPINE DERIVATIVES AND THEIR USE AS AMPA-RECEPTOR INHIBITORS

This application is a national stage entry under 35 U.S.C. § 371 PCT/DE97/00225, filed Jan. 29, 1997.

The invention relates to new 8-alkoxy-substituted 2,3-benzodiazepine derivatives, their production and use as pharmaceutical agents.

It is already known that selected 2,3-benzodiazepine derivatives have modulatory activity at quisqualate receptors and owing to this property are suitable as pharmaceutical agents for treating diseases of the central nervous system.

It has now been found that 8-alkoxy-substituted 2,3-benzodiazepine derivatives are distinguished by better properties compared to the known compounds.

The invention relates to the compounds of formula I (I)

in which
X means hydrogen or halogen,
Y means —$NR^3$— or —N=,
$R^1$ and $R^2$ are the same or different and mean hydrogen, $C_1$–$C_6$ alkyl, nitro, halogen, the group —$NR^8R^9$, —O—$C_{1-4}$ alkyl, —$CF_3$, —OH, $C_{1-6}$ alkanoyloxy,
$R^3$ means hydrogen, the group —CO—$R^{10}$, $C_{1-6}$ alkyl or $C_{3-7}$ cycloalkyl,
$R^4$ means optionally substituted $C_1$–$C_6$ alkyl,
$R^5$ means hydrogen or
$R^4$ and $R^5$ together mean oxygen,
$R^6$ means $C_{1-4}$ alkyl,
$R^8$ and $R^9$ are the same or different and mean hydrogen, $C_1$–$C_6$ alkyl or —CO–$C_{1-6}$ alkyl,
$R^{10}$ means hydrogen, optionally substituted $C_1$–$C_6$ alkyl, optionally substituted $C_{6-10}$ aryl, the group —$NR^{11}R^{12}$, —O—$C_{1-6}$ alkyl, $C_{3-7}$ cycloalkyl, $C_{2-6}$ alkenyl or —O—$C_{3-7}$ cycloalkyl,
$R^{11}$ and $R^{12}$ are the same or different and mean hydrogen, optionally substituted $C_1$–$C_6$ alkyl or optionally substituted $C_{6-10}$ aryl and
—C...C... means a double bond or single bonds
as well as their isomers and physiologically compatible salts.

Alkyl is defined in each case as a straight-chain or branched alkyl radical, such as, for example, methyl, ethyl, propyl, isopropyl, butyl, isobutyl, sec-butyl, tert-butyl, pentyl, isopentyl or hexyl. As substituents of the alkyl radical, $C_1$–$C_6$ alkoxy or halogen can be mentioned.

If a halogenated alkyl radical is present, the latter can be halogenated or perhalogenated in one or more places.

Halogen is defined as fluorine, chlorine, bromine and iodine.

As an aryl radical, for example, naphthyl and preferably phenyl can be mentioned. The substituent is, for example, $C_{1-6}$ alkoxy or halogen.

Cycloalkyl is defined in each case as cyclopropyl, cyclobutyl, cyclopentyl, cyclohexyl and cycloheptyl, especially $C_{3-5}$ cycloalkyl.

The alkenyl radicals can be straight-chain or branched. For example, 1-propenyl, 2-propenyl, 3-methyl-2-propenyl, 1-butenyl, 2-butenyl, methallyl and vinyl can be mentioned.

As alkanoyl radicals, straight-chain or branched aliphatic carboxylic acid radicals, such as formyl, acetyl, propionyl, butanoyl, isopropylcarbonyl, caproyl, valeroyl, trimethylacetyl, i.a., are suitable.

The physiologically compatible salts are derived from inorganic and organic acids. Suitable are inorganic acids, such as, for example, hydrohalic acids such as hydrochloric acid, hydrobromic acid, phosphoric acid, sulfuric acid or organic acids, such as, for example, aliphatic or aromatic mono- or dicarboxylic acids such as formic acid, acetic acid, maleic acid, fumaric acid, succinic acid, lactic acid, tartaric acid, citric acid, oxalic acid, glyoxylic acid or sulfonic acids, for example, $C_{1-4}$ alkanesulfonic acids such as methanesulfonic acid or benzenesulfonic acids that are optionally substituted by halogen or $C_{1-4}$ alkyl, such as p-toluenesulfonic acid.

The compounds of formula I also comprise the possible tautomeric forms, the E- or Z-isomers, or, if chiral centers are present, the diastereomers and their mixtures and the racemates and enantiomers.

Preferred compounds of general formula I are those in which $R^1$ means amino or nitro and $R^2$ means hydrogen.

The compounds of general formula I as well as their physiologically compatible salts can be used as pharmaceutical agents owing to their non-competitive inhibition of the AMPA receptors. Owing to their profile of action, the compounds according to the invention are suitable for treating diseases that are caused by hyperactivity of excitatory amino acids, such as, for example, glutamate or aspartate. Since the new compounds act as non-competitive antagonists of excitatory amino acids, they are suitable especially for treating those diseases that are influenced by the receptors of excitatory amino acids, especially the AMPA receptor.

The pharmacological action of the compounds of formula I was determined by means of the tests described below:

Male NMRI mice weighing 18–22 g were kept under controlled conditions (0600–1800 hours light/dark cycle, with free access to food and water) and their assignment to groups was randomized. The groups consisted of 5–16 animals. The observation of the animals was performed between 0800 and 1300 hours.

AMPA was sprayed into the left ventricles of mice that were allowed to move freely. The applicator consisted of a cannula with a device made of stainless steel, which limits the depth of injection to 3.2 mm. The applicator was connected to an injection pump. The injection needle was inserted perpendicular to the surface of the skull according to the coordinates of Montemurro and Dukelow. The animals were observed up to 180 seconds until clonic or tonic seizures set in. The clonic movements, which last longer than 5 seconds, were counted as seizures. The beginning of the clonic seizures was used as an endpoint for determining the seizure threshold. The dose that was necessary to raise or reduce the seizure threshold by 50% ($THRD_{50}$) was determined in 4–5 experiments. The $THRD_{50}$ and the confidence limit were determined in a regression analysis.

The results of these tests show that the compound of formula I and its acid addition salts influence functional disorders of the AMPA receptor. They are therefore suitable for the production of pharmaceutical agents for symptomatic and preventive treatment of diseases that are triggered by changing the function of the AMPA receptor complex.

The treatment with the compounds according to the invention prevents or delays the cell damage that occurs as a result of disease and functional disorders and reduces the concomitant symptoms.

According to the invention, the compounds can be used for treating neurological and psychiatric disorders that are triggered by overstimulation of the AMPA receptor. The neurological diseases, which can be treated functionally and preventatively, include, for example, neurodegenerative disorders such as Parkinson's disease, Alzheimer's disease, Huntington's chorea, amyotropic lateral sclerosis, and olivopontocerebellar degeneration. According to the invention, the compounds can be used for the prevention of postischemic cellular degeneration, cellular degeneration after brain trauma, in the case of stroke, hypoxia, anoxia and hypoglycemia and for the treatment of senile dementia, AIDS dementia, neurological symptoms that are related to HIV infections, multiinfarct dementia as well as epilepsy and muscle spasms. The psychiatric diseases include anxiety conditions, schizophrenia, migraines, pain conditions as well as the treatment of sleep disorders and withdrawal symptoms after drug abuse such as in alcohol, cocaine, benzodiazepine or opiate withdrawal. In addition, the compounds can be used in the prevention of tolerance development during long-term treatment with sedative pharmaceutical agents, such as, for example, benzodiazepines, barbiturates and morphine. Moreover, the compounds can be used as anesthetics (anesthesia), analgesics or anti-emetics.

For use of the compounds according to the invention as pharmaceutical agents, the latter are brought into the form of a pharmaceutical preparation, which in addition to the active ingredient for enteral or parenteral administration contains suitable pharmaceutical, organic or inorganic inert media, such as, for example, water, gelatin, gum arabic, lactose, starch, magnesium stearate, talc, vegetable oils, polyalkylene-glycols, etc. The pharmaceutical preparations can be present in solid form, for example, as tablets, coated tablets, suppositories, capsules or in liquid form, for example as solutions, suspensions or emulsions. Moreover, they optionally contain adjuvants such as preservatives, stabilizers, wetting agents or emulsifiers, salts for changing the osmotic pressure or buffers.

For parenteral use, especially injection solutions or suspensions, especially aqueous solutions of the active compounds in polyhydroxyethoxylated castor oil, are suitable.

As vehicle systems, surface-active adjuvants such as salts of bile acids or animal or vegetable phospholipids, but also mixtures of them as well as liposomes or their components can also be used.

For oral use, especially tablets, coated tablets or capsules with talc and/or hydrocarbon vehicles or binders, such as, for example, lactose, corn or potato starch, are suitable. The substance may also be administered in liquid form, such as, for example, as juice, to which optionally a sweetener is added.

The dosage of the active ingredients can vary depending on method of administration, age and weight of the patient, type and severity of the disease to be treated and similar factors. The daily dose is 0.5–1000 mg, preferably 50–200 mg, whereby the dose can be given as a single dose to be administered once or divided into two or more daily doses.

The production of the compounds according to the invention is carried out for example, in that a) a compound of formula II

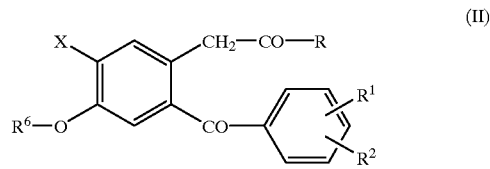

in which $R^1$, $R^2$, $R^6$ and X have the above meaning and R is hydroxy or $C_{1-6}$ alkyl, is cyclized with $H_2$—NH—$R^3$ or b) a compound of formula III

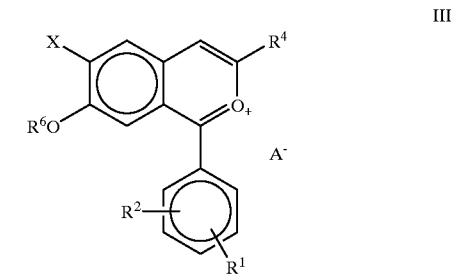

in which $R^1$, $R^2$, $R^4$, $R^6$ and X have the above meaning and $A^-$ means an anion of an inorganic base, is reacted with $H_2N$—$NHR^3$ and optionally then the nitro group and/or the 3,4-double bond is reduced and/or a compound of general formula I is converted by reduction, dehalogenation, acylation, alkylation, hydroxylation, halogenation, introduction of a carbamoyl group or an ester group into another compound of general formula I, the isomers are separated or the salts are formed.

The production of the compounds of formula I according to process step a) is carried out by reaction of the diketones of formula II with hydrazine hydrate or corresponding hydrazine derivatives in polar solvents such as alcohols or methylene chloride in one stage or without isolation of the hydrazone suitably at a higher temperature.

As anions, according to process variant b), halides such as chloride, bromide, iodide, tetrafluoroborate, tetrachloroferrate, hexachlorostannate, sulfhydrate, phosphate and perchlorate are suitable. The compounds according to the invention are obtained preferably by reaction of 2-benzopyrilium-perchlorate with hydrazine hydrate or hydrazine derivatives in polar solvents such as alcohols or dimethylformamide at room temperature or a higher temperature.

The reduction in the nitro group is performed in polar solvents at room temperature or a higher temperature. As catalysts for reduction, metals such as Raney nickel or noble metal catalysts such as palladium or platinum optionally on vehicles are suitable. Instead of hydrogen, for example, ammonium formate or hydrazine can also be used in a known way. Reducing agents such as tin(II) chloride or titanium(III) chloride can also be used as complex metal hydrides optionally in the presence of heavy metal salts. Iron can also be used as a reducing agent. The reaction is then performed in the presence of an acid such as, e.g., acetic acid or ammonium chloride, optionally with the addition of a solvent, such as, for example, water or methanol. If Raney nickel is used for the reduction, generally no dehalogenation of substituent X takes place. If a simultaneous dehalogenation and reduction of the nitro group is desired, it is suitable to use noble metal catalysts such as palladium or platinum and an acid-binding agent, such as, e.g., potassium carbonate. As a hydrogen source, hydrogen gas or, e.g., hydrazine hydrate can be used. In the latter case, the reaction can suitably be performed at a higher temperature.

The acylation can be performed with or without solvent at room temperature or a higher temperature with the commonly used acylating agents. As acylating agents, anhydrides or acid halides are suitable. As anhydrides, mixed or else symmetrical anhydrides can be used. carbamoyl derivatives are suitably obtained by acylation with a corresponding isocyanate. If the acylation is performed with chloroformic acid esters such as chloroformic acid phenyl ester, the corresponding carbamoyl compounds are obtained by subsequent reaction with primary and secondary organic amines such as methylamine or the corresponding ester group can be introduced by reaction with alcohols such as methanol, ethanol in the presence of catalytic amounts of NaCN or with titanium tetraisopropylate in the presence of the alcohol that is desired for re-esterification.

If alkylation of an amino group is desired, it can be alkylated according to commonly used methods—for example with alkyl halides—or according to the Mitsonubo variant by reaction with an alcohol in the presence of triphenylphosphine and azodicarboxylic acid ester, or the amine can be subjected to reductive amination with aldehydes or ketones optionally in succession with two different carbonyl compounds, whereby mixed derivatives are obtained [Bibliography, e.g., Verardo et al. Synthesis (1993), 121; Synthesis (1991), 447; Kawaguchi, Synthesis (1985), 701; Micovic et al. Synthesis (1991), 1043].

The acylation of an amino group is carried out in the usual way, for example, with an acid halide or acid anhydride optionally in the presence of a base such as dimethylaminopyridine in solvents such as methylene chloride, tetrahydrofuran or pyridine, according to the Schotten-Baumann variant in aqueous solution at weakly alkaline pH or by reaction with an anhydride in glacial acetic acid.

The introduction of the halogens chlorine, bromine or iodine via the amino group can be carried out, for example, also according to Sandmeyer, by the diazonium salts that are intermediately formed with nitrites being reacted with copper(I) chloride or copper(I) bromide in the presence of the corresponding acid such as hydrochloric acid or hydrobromic acid or with potassium iodide.

Instead of diazonium salts, triazenes optionally also can be used. If an organic nitrite is used, the halogen can be introduced into a solvent such as, for example, dimethylformamide, e.g., by the addition of methylene iodide or tetrabromomethane. The removal of the amino group can be achieved either by reaction with an organic nitrite in tetrahydrofuran or by diazotization and reductive boiling-down of diazonium salt with, for example, phosphorous acid optionally with the addition of copper(I) oxide. The introduction of fluorine is possible, for example, by Balz Schiemann reaction of diazonium tetrafluoroborate, or according to J. Fluor. Chem. 76, 1996, 59–62 by diazotization in the presence of HFx pyridine and subsequent boiling-down optionally in the presence of a fluoride ion source such as, e.g., tetrabutylammonium fluoride.

The replacement of the amino group by the hydroxy group is carried out according to methods that are known in the literature, preferably by conversion into triazene and subsequent treatment with a strongly acidic ion exchanger (according to Tetr. Letters 1990, 4409 E, J.-R. Barrio et al. J. Chem. Soc. Chem. Comun., 443 (1983)).

The isomer mixtures can be separated according to the commonly used methods, such as, for example, crystallization, chromatography or salt formation, into enantiomers or E/Z-isomers.

The production of salts is carried out in the usual way by a solution of the compound of formula I being mixed with the equivalent amount of acid or excess acid, which optionally is in solution, and the precipitate being separated or the solution being worked up in the usual way.

In so far as the production of the starting compounds is not described, the latter are known, or it is carried out analogously to known compounds. The new compounds of formula I are also suitable as intermediate products for the production of pharmacologically active compounds.

The following examples explain the production of the compounds according to the invention.

EXAMPLE 1

1-(4-Aminophenyl)-8-methoxy-4,5-dihydro-3H-2,3-benzodiazepin-4-one

Step A 5.0 g (130.0 mmol) of sodium borohydride is added to a suspension of 8.30 g (75.0 mmol) of powdered calcium chloride in anhydrous THF at 0° C., and after 30 minutes of stirring, a solution of 10.75 g (39.35 mmol) of 3-bromo-4-methoxy-phenylacetic acid methyl ester (O. N. Tolkachev i.a., Zh. Obshsh. Khim. 31 (1961), 1540–1545) in 75 ml of THF is added in drops. Then, the mixture is stirred for 1 hour at 0° C., then for 20 hours at room temperature and again cooled to 0° C. 100 ml of water and 100 ml of 1N HCl are added, and the THF is drawn off. The remaining residue is extracted with ethyl acetate, and the organic phase is washed with water, dried and concentrated by evaporation.

9.10 g (100%) of 2-(3-bromo-4-methoxy-phenyl)-ethanol is obtained as a crude product, which is processed in this form in the next step.

Step B

Hydrogen chloride gas that is dried for 5 hours is introduced into a suspension of 7.50 g (32.4 mmol) of 2-(3-bromo-4-methoxy-phenyl)-ethanol, 4.90 g (32.4 mmol) of 4-nitro-benzaldehyde and 4.39 g (32.4 mmol) of freshly melted zinc chloride in anhydrous benzene (96 ml). The reaction mixture is then diluted with ethyl acetate and washed neutral with water. After drying and concentration by evaporation, the solid residue is recrystallized from ethyl acetate (25 ml). 7.91 g (67%) of 6-bromo-7-methoxy-1-(4-nitrophenyl)-isochroman, melting point 144–147° C., is obtained.

Step C 5.46 g (15.0 mmol) of the compound of Step B is stirred overnight in acetone (110 ml) with 22.5 ml of Jones reagent. The precipitated salt is filtered and rewashed with acetone. The salt is then stirred with 4 ml of isopropanol for 30 minutes and again filtered off. The combined organic filtrates are concentrated by evaporation. The residue is then dissolved in ethyl acetate, washed neutral with water, and the organic phase is dried and concentrated by evaporation. The crystalline residue is recrystallized from ethyl acetate (12 ml). 4.30 g (73%) of 5-bromo-4-methoxy-2-(4-nitrobenzoyl)-phenylacetic acid with a melting point of 189–192° C. is obtained.

Step D 3.94 g (10.0 mmol) of the substance of Step C is dissolved in 75 ml of ethanol. After 1.50 ml (30 mmol) of 98% hydrazine hydrate is added, the mixture is heated to boiling for 5 hours. After cooling, the solution is acidified with 20 ml of 1N HCl and concentrated by evaporation in a vacuum. The residue is suspended in 8 ml of water, and the crystalline hydrazone is washed with water and dried in a vacuum.

The hydrazone is then suspended in dry methylene chloride and mixed with a solution of 2.06 g (10.0 mmol) of N,N'-dicyclohexylcarbodiimide in 30 ml of methylene chloride and stirred for 16–20 hours. The product is suctioned off, then heated to boiling with ethanol (24 ml) for 10–15 minutes and filtered again. 2.56 g (66%) of 7-bromo-8-methoxy-1-(4-nitrophenyl)-4,5-dihydro-3H-2,3-benzodiazepin-4-one with a melting point of 245–256° C. is obtained.

Produced analogously is:

7-Bromo-8-methoxy-1-phenyl-4,5-dihydro-3H-2,3-benzodiazepin-4-one

Step E 1.10 g (2.82 mmol) of the previously described compound is dissolved in 40 ml of methylene chloride and 50 ml of methanol and, after 0.39 g (2.82 mmol) of potassium carbonate and 0.20 g of 10% palladium/activated carbon are added, it is hydrogenated. Then, catalyst is suctioned out, and the filtrate is concentrated by evaporation. The residue is dissolved in chloroform and washed several times with water. After repeated concentration by evaporation, the product is heated to boiling with ethanol and filtered. 0.62 g (78%) of 1-(4-aminophenyl)-8-methoxy-4,5-dihydro-3H-2,3-benzodiazepin-4-one, melting point 167–170° C., is obtained.

Produced analogously from the corresponding 7-bromine compound is 8-methoxy-1-phenyl-4,5-dihydro-3H-2,3-benzodiazepin-4-one

EXAMPLE 2

1-(4-Aminophenyl)-7-chloro-8-methoxy-4,5-dihydro-3H-2,3-benzodiazepin-4-one

Step A

Hydrogen chloride gas that is dried for 7 hours is introduced into a suspension of 15.70 g (72.0 mmol) of 2-(3-chloro-4-methoxyphenyl)-ethanol (L. S. Fosdick i.a., J. Am. Chem. Soc. 68 (1946), 840–843), 10.23 g (72.0 mmol) of nitrobenzaldehyde and 9.18 g (72 mmol) of freshly melted zinc chloride in anhydrous benzene (200 ml). Then, the reaction mixture is diluted with ethyl acetate and washed neutral with water, dried and concentrated by evaporation. The residue is recrystallized from ethyl acetate (60 ml). 10.4 g (45%) of 6-chloro-7-methoxy-1-(4-nitrophenyl)-isochroman, melting point 150–153° C., is obtained.

Step B 10.23 g (32.0 mmol) of the substance of the preceding step is mixed with 55 ml of Jones reagent. The procedure is as in Step C of Example 1, and the crude product that is obtained is recrystallized from acetic acid. 7.28 g (68%) of 5-chloro-4-methoxy-2-(4-nitrobenzoyl)-phenylacetic acid with a melting point of 185–188° C. is obtained.

Step C 5.32 g (16.0 mmol) of the above compound is mixed in 120 ml of ethanol with 2.40 ml (50 mmol) of 98% hydrazine hydrate, and it is heated to boiling for 5 hours. Then, the procedure is as in Step D of Example 1. The crude product is purified by repeated heating in ethanol. 3.48 g (63%) of 7-chloro-8-methoxy-1-(4-nitrophenyl)-4,5-dihydro-3H-2,3-benzodiazepin-4-one with a melting point of 258–262° C. is obtained.

Step D 0.48 g (1.4 mmol) of the compound of the preceding step is dissolved in 10 ml of DMF and 10 ml of methanol, and 0.27 ml (5.5 mmol) of 98% hydrazine hydrate is added in the presence of Ra/Ni catalyst. The mixture is then stirred for 2 hours. Catalyst is suctioned out, and the filtrate is concentrated by evaporation in a vacuum. The residue is suspended in water, and the product is filtered. 0.31 g (70%) of 1-(4-aminophenyl)-7-chloro-8-methoxy-4,5-dihydro-3H-2,3-benzodiazepin-4-one, melting point 234–236° C., is obtained.

EXAMPLE 3

1-(4-Aminophenyl)-4-methyl-8-methoxy-5H-2,3-benzodiazepine

Step A 18.04 g (132.4 mmol) of freshly melted zinc chloride is added to a solution of 32.46 g (132.4 mmol) of 1-(3-bromo-4-methoxyphenyl)-propan-2-ol and 20.01 g (132.4 mmol) of 4-nitrobenzaldehyde in 166 ml of dry benzene, and then dry hydrogen chloride gas is introduced for 3 hours. The reaction mixture is then heated to boiling for 1 hour and stirred with 150 ml of water. The organic phase is separated and washed in succession with water (2×50 ml), 20% sodium hydrogen sulfite solution (100 ml), 8% sodium bicarbonate solution (50 ml) and water (2×50 ml) and dried. After concentration by evaporation, a thick oil, which during treatment with hot ethanol (450 ml) yields crystalline 6-bromo-3-methyl-7-methoxy-1-(4-nitrophenyl)-isochroman, is obtained: 20.39 g (41%), melting point 128–129° C.

Step B 70.78 ml (188.6 mmol) of Jones reagent is added in drops to a solution of 20.39 g (53.9 mmol) of the compound of Step A in 250 ml of acetone at 20° C. for about 20 minutes. The reaction mixture is then stirred for another 4 hours and then mixed with water (750 ml). The precipitated substance is suctioned off and washed with water. The crude product that is obtained (20.32 g) is dissolved in ethyl acetate (203 ml) and mixed with 4.9 ml (56.3 mmol) of 70% perchloric acid. The solution is heated for several minutes to boiling, whereby crystals begin to precipitate. After cooling, the product is suctioned off and washed with ethyl acetate. 11.26 g (44%) of 6-bromo-3-methyl-7-methoxy-1-(4-nitrophenyl)-2-benzopyrilium perchlorate with a melting point of 252–253° C. (decomposition) is obtained.

Step C 4.08 g (8.59 mmol) of the 2-benzopyrilium salt of Step B is dissolved in DMF (20 ml) and mixed with 1.29 ml (25.7 mmol) of 98% hydrazine hydrate. After stirring at 25° C. for 15 minutes, the product is precipitated with 80 ml of water. After suctioning off and washing with water, 3.32 g of 7-bromo-8-methoxy-4-methyl-1(4-nitrophenyl)-5H-2,3-benzodiazepine is obtained as a crude product, melting point 218–221° C. (decomposition). After one-time recrystallization from 15 ml of ethanol, 2.96 g (89%) of the product in the form of yellow crystals with melting point 234–236° C. (decomposition) is obtained.

Produced in a basically similar way via corresponding stages A–C is 7-bromo-8-methoxy-4-methyl-1-phenyl-5H-2,3-benzodiazepine Step D 0.50 g (1.28 mmol) of the benzodiazepine derivative from preceding Step C is suspended in methyl cellosolve (50 ml). After 0.27 g (1.89 mmol) of dry potassium carbonate, 0.50 g of palladium on carbon (10%) and 0.2 ml of hydrazine hydrate (98%) are added, the mixture is stirred for 1 hour at 100° C. Solid is suctioned out, and the filtrate is concentrated by evaporation. The oily residue is brought to crystallization with water. The crude product is recrystallized from ethanol (3.5 ml), whereby 0.21 g (59%) of the title compound in the form of almost white crystals with a melting point of 136–138° C. is obtained.

Produced analogously from the corresponding 7-bromine compound is:

8-Methoxy-4-methyl-1-phenyl-5H-2,3-benzodiazepine

EXAMPLE 4

3-Acetyl-1-(4-aminophenyl)-4-methyl-8-methoxy-4,5-dihydro-3H-2,3-benzodiazepine

Step A 3.5 ml (43.2 mmol) of concentrated hydrochloric acid is first added, and then over about 10 minutes, 1.80 g (47.5 mmol) of sodium borohydride is added in portions to a suspension of 1.4 g (3.6 mmol) of 7-bromo-4-methyl-8-methoxy-1-(4-nitrophenyl)-5H-2,3-benzodiazepine (Example 3, Step C) in 60 ml of methanol. The suspension is stirred for another hour, and then diluted with water (60 ml). The crystalline material is suctioned off and washed with 50% aqueous methanol (3×50 ml). The 7-bromo-4-methyl-8-methoxy-1-(4-nitrophenyl)-4,5-dihydro-3H-2,3-benzodiazepine that is obtained as a crude product is further purified by suspension in 8 ml of hot ethanol. After suctioning-off, 1.23 g (88%) of chrome yellow crystals with a melting point of 172–174° C. is obtained.

Produced analogously is:

7-Bromo-4-methyl-8-methoxy-1-phenyl-4,5-dihydro-3H-2,3-benzodiazepine

Step B 0.60 g (1.5 mmol) of the dihydro compound from the preceding Step A is dissolved in 3 ml of acetic anhydride. After one hour of reaction time at 25° C., the solution is stirred with 15 ml of water, and the precipitated crystals are suctioned off and washed with water (4×5 ml). After recrystallization from ethanol (32 ml), the 3-acetyl-7-bromo-4-methyl-8-methoxy-1-(4-nitrophenyl)-4,5-dihydro-3H-2,3-benzodiazepine that is isolated as a crude product yields 0.56 g (86%) of pure product in the form of yellow crystals with a melting point of 194–196° C.

Produced analogously is:

3-Acetyl-7-bromo-4-methyl-8-methoxy-1-phenyl-4,5-dihydro-3H-2,3-benzodiazepine

Step C 0.54 g (1.2 mmol) of the acetyl derivative of the preceding Step B is reduced according to Example 3, Step D. 0.36 g of the title compound is obtained as a crude product. Further purification is carried out by column chromatography on silica gel with the eluant chloroform:methanol=95:5. Recrystallization of the product from 12 ml of ethanol yields 0.16 g (67%) of the title compound as yellow crystals, melting point 237–238° C.

Produced in a basically similar way from the corresponding 7-bromine compounds are:

3-Methoxycarbonyl-1-(4-aminophenyl)-4-methyl-8-methoxy-4,5-dihydro-3H-2,3-benzodiazepine 3-acetyl-4-methyl-8-methoxy-1-phenyl-4,5-dihydro-3H-2,3-benzodiazepine

EXAMPLE 5

1-(4-Aminophenyl)-4-methyl-3-methylcarbamoyl-8-methoxy-4,5-dihydro-3H-2,3-benzodiazepine Step A 0.60 g (1.5 mmol) of 7-bromo-4-methyl-8-methoxy-1-(4-nitrophenyl)-4,5-dihydro-3H-2,3-benzodiazepine (Example 4, Step A) is dissolved in 12 ml of dry methylene chloride and mixed with 0.64 ml (10.5 mmol) of methyl isocyanate. After a reaction period of 9 days at 25° C., the solution is concentrated by evaporation, and the residue is recrystallized from ethanol (10 ml). 0.56 g (83%) of 7-bromo-4-methyl-3-methylcarbamoyl-8-methoxy-1-(4-nitrophenyl)-4,5-dihydro-3H-2,3-benzodiazepine in the form of yellow crystals with a melting point of 224–226° C. is obtained.

Produced analogously is:

7-Bromo-4-methyl-3-methylcarbamoyl-8-methoxy-1-phenyl-4,5-dihydro-3H-2,3-benzodiazepine Step B 0.54 g (1.2 mmol) of the nitro compound of the above Step A is reduced according to Example 3, Step D. 0.32 g of the title compound is obtained as a crude product, which is further purified by column chromatography (silica gel, eluant ethyl acetate:benzene=4:1). After the fractions are concentrated by evaporation, the product is recrystallized from ethyl acetate, and 0.20 g (49%) of the pure title compound with a melting point of 190–191° C. is obtained.

Produced analogously is:

8-Methoxy-4-methyl-3-methylcarbamoyl-1-phenyl-4,5-dihydro-3H-2,3-benzodiazepine

EXAMPLE 6

1-(4-Aminophenyl)-7-chloro-4-methyl-8-methoxy-5H-2,3-benzodiazepine

Step A

A solution of 21.16 g (105.4 mmol) of 1-(3-chloro-4-methoxyphenyl)-2-hydroxypropane in 106 ml of dry benzene is mixed with 15.93 g (105.4 mmol) of 4-nitrobenzaldehyde and 14.36 g (105.4 mmol) of freshly melted zinc chloride, and dry hydrogen chloride gas is introduced for 3 hours. Then, the mixture is heated to boiling for 30 minutes. Working-up is carried out according to the process that is described in Example 3, Step A. The 6-chloro-3-methyl-7-methoxy-1-(4-nitrophenyl)-isochroman that is obtained is first isolated as an oily crude product, which crystallizes during treatment, however, with 370 ml of hot ethanol: 15.79 g (50%, melting point 118–120° C.

Step B 16.75 g (50.1 mmol) of the isochroman derivative from the preceding Step A is oxidized according to the process of Step B of Example 3 according to Jones. The crude product is treated in 165 ml of hot ethyl acetate with 4.56 ml (52.47 mmol) of 70% perchloric acid, and 12.09 g of crude 6-chloro-3-methyl-7-methoxy-1-(4-nitrophenyl)-2-benzopyrilium perchlorate, which yields 10.25 g (48%) of yellow crystals of the pure product with a melting point of 244–246° C. after suspension in hot glacial acetic acid (60 ml), is obtained.

Step C 2.74 ml (54.7 mmol) of hydrazine hydrate is added to a suspension of 10.15 g (23.8 mmol) of the perchlorate salt of the preceding Step B in 103 ml of isopropanol. The reaction mixture is heated to boiling for 30 minutes, and after cooling, the precipitated product is suctioned off, and it is washed with isopropanol. The crude 7-chloro-4-methyl-8-methoxy-1-(4-nitrophenyl)-5H-2,3-benzodiazepine (6.13 g) that is obtained is further purified by stirring in 60 ml of boiling water. 4.71 g (58%) of yellow crystals with a melting point of 234–236° C. is obtained.

Step D

A suspension of 0.24 g (0.7 mmol) of the benzodiazepine of Step C in 24 ml of methanol is mixed with Ra/Ni catalyst and 0.075 ml (1.54 mmol) of 98% hydrazine hydrate. Then, the mixture is stirred for one more hour, whereby vigorous hydrogen development occurs. Catalyst is suctioned out, and the filtrate is concentrated by evaporation. The resulting oil is brought to crystallization by pasting with water. After recrystallization from ethanol (4 ml), 0.16 g (73%) of the title compound with a melting point of 198–200° C. is obtained.

EXAMPLE 7

3-Cyclopropylcarbonyl-1-(4-aminophenyl)-4-methyl-8-methoxy-3H-2,3-benzodiazepine Step A 0.5 g of 7-bromo-1-(4-nitrophenyl)-4-methyl-8-methoxy-5H-2,3-benzodiazepine (Example 3, Step C) is suspended in 15 ml of benzene, mixed with 0.53 g of potassium carbonate and 0.17 ml of cyclopropylcarboxylic acid chloride and then refluxed for 5 hours. Then, the mixture is stirred with water, the organic phase is separated, washed in succession with soda solution and water, dried, filtered and concentrated by evaporation. The residue is purified by absorptive precipitation in ethanol, and 0.38 g of 7-bromo-3-cyclopropylcarbonyl-1-(4-nitrophenyl)-4-methyl-8-methoxy-3H-2,3-benzodiazepine of the title compound with a melting point of 231–223° C. is obtained.

Step B 0.38 mg (0.83 mmol) of the nitro compound of Step A is reduced according to Example 2, Step D. 0.31 g (87%) of 1-(4-aminophenyl)-7-bromo-3-cyclopropylcarbonyl-4-methyl-8-methoxy-3H-2,3-benzodiazepine with a melting point of 224–226° C. is obtained.

Step C 0.31 g (0.73 mmol) of the aminophenyl compound of Step C is dissolved in 50 ml of methanol and after 0.31 g of palladium on carbon (10%) and 0.20 g (1.45 mmol) of potassium carbonate are added, it is catalytically hydrogenated for three days. After catalyst is suctioned out, it is concentrated by evaporation, and the residue is pulverized with water. The crude product that is obtained is purified by column chromatography on silica gel with ethyl acetate:benzene=1:1 as an eluant. 0.14 g of the title compound with a melting point of 214–216° C. is obtained.

Produced analogously are:

3-Acetyl-1-(4-aminophenyl)-4-methyl-8-methoxy-3H-2,3-benzodiazepine 3-n-propionyl-1-(4-aminophenyl)-4-methyl-8-methoxy-3H-2,3-benzodiazepine 3-acetyl-8-methoxy-4-methyl-1-phenyl-3H-2,3-benzodiazepine 3-cyclopropylcarbonyl-8-methoxy-4-methyl-1-phenyl-3H-2,3-benzodiazepine

EXAMPLE 8

1-(4-Aminophenyl)-8-methyl-4-methyl-3-propionyl-4,5-dihydro-3H-2,3-benzodiazepine Step A 0.67 g (1.7 mmol) of 7-bromo-8-methoxy-4-methyl-1-(4-nitrophenyl)-4,5-dihydro-3H-2,3-benzodiazepine (Example 4, Step A) is suspended in 3.35 ml of propionic acid anhydride and stirred for 3 hours at room temperature. The mixture is diluted with water, and the product is filtered. After washing with water and drying by column chromatography, the crude product is purified (silica gel, eluant benzene:ethyl acetate: 4:0.2). 0.53 g (70%) of 7-bromo-8-methoxy-4-methyl-1-(4-nitrophenyl)-3-propionyl-3H-2,3-benzodiazepine is obtained as a thick oil.

Step B 0.53 g (1.18 mmol) of the propionyl derivative of Step A is reduced according to Example 3, Step D. 0.35 g of the title compound is obtained as a crude product, which is further purified by column chromatography (silica gel, eluant ethyl acetate:benzene=4:1). After recrystallization from ethanol, the product is 0.14 g (35%) of pure title compound with a melting point of 166–168° C.

EXAMPLE 9

1-(4-Aminophenyl)-3-cyclopropylcarbonyl-8-methoxy-4-methyl-4,5-dihydro-3H-2,3-benzodiazepine Step A 0.69 g (1.77 mmol) of 7-bromo-8-methoxy-4-methyl-1-(4-nitrophenyl)-4,5-dihydro-3H-2,3-benzodiazepine (Example 4, Step A) is acylated in methylene chloride (15 ml) in the presence of 0.29 ml (2.1 mmol) of triethylamine with 0.19 ml (2.1 mmol) of cyclopropanoic acid chloride at room temperature for 1.5 hours. After concentration by evaporation and suspension with water, 0.78 g of a crude product, which is purified by suspension in hot ethanol, is obtained. 0.75 g (93%) of 7-bromo-3-cyclopropylcarbonyl-8-methoxy-4-methyl-1-(4-nitrophenyl)-4,5-dihydro-3H-2,3-benzodiazepine with a melting point of 194–196° C. is obtained.

Step B

Reduction and dehalogenation are carried out from 0.73 g (1.59 mmol) of the compound of Step A according to Example 3, Step D, and 0.51 g of the title compound is thus obtained as a crude product. After column chromatography (silica gel, eluant ethyl acetate:benzene: 4:1), the product is recrystallized from ethyl acetate, and 0.36 g (65%) of the title compound with a melting point of 93–95° C. is thus obtained.

What is claimed is:

1. A compound of formula I

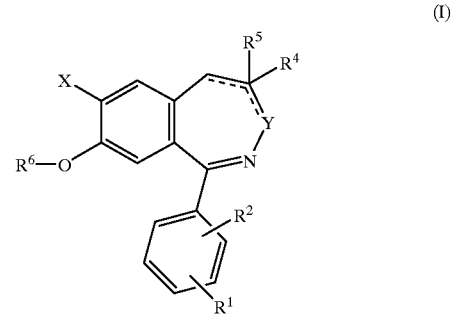

in which

X means hydrogen or halogen,

Y means —$NR^3$— or —N=, $R^1$ and $R^2$ are the same or different and mean hydrogen, $C_1$–$C_6$ alkyl, nitro, halogen, the group —$NR^8R^9$, —O—$C_{1-4}$ alkyl, —$CF_3$, OH or $C_{1-6}$ alkanoyloxy, $R^3$ means hydrogen, the group —CO—$R^{10}$, $C_{1-6}$ alkyl or $C_{3-7}$ cycloalkyl, $R^4$ means optionally substituted $C_1$–$C_6$ alkyl, $R^5$ means hydrogen or $R^4$ and $R^5$ together mean oxygen, $R^6$ means $C_{1-4}$ alkyl, R⁸ and R⁹ are the same or different and mean hydrogen, $C_1$–$C_6$ alkyl or —CO—$C_{1-6}$ alkyl R¹⁰ means hydrogen, optionally substituted $C_1$–$C_6$ alkyl, optionally substituted $C_{6-10}$ aryl, the group —NR¹¹R¹², —O—$C_{1-6}$ alkyl, $C_{3-7}$ cycloalkyl, $C_{2-6}$ alkenyl or —O—$C_{3-7}$ cycloalkyl, R¹¹ and R¹² are the same or different and mean hydrogen, optionally substituted $C_1$–$C_6$ alkyl or optionally substituted $C_{6-10}$ aryl and —C⸗C⸗ means a double bond or single bonds or an isomer or physiologically compatible salt thereof
with the proviso that the compound is not 1-(3-chlorophenyl)-4-methyl-8-methoxy, 5H-2,3-benzodiazepine.

2. 1-(4-Aminophenyl)-8-methoxy-4,5-dihydro-3H-2,3-benzodiazepin-4-one
1-(4-aminophenyl)-4-methyl-8-methoxy-5H-2,3-benzodiazepine,
3-acetyl-1-(4-aminophenyl)-4-methyl-8-methoxy-4,5-dihydro-3H-2,3-benzodiazepine,
3-n-propionyl-1-(4-aminophenyl)-4-methyl-8-methoxy-4,5-dihydro-3H-2,3-benzodiazepine,
3-cyclopropylcarbonyl-1-(4-aminophenyl)-4-methyl-8-methoxy-4,5-dihydro-3H-2,3-benzodiazepine,
3-methoxycarbonyl-1-(4-aminophenyl)-4-methyl-8-methoxy-4,5-dihydro-3H-2,3-benzodiazepine,
3-methylcarbamoyl-1-(4-aminophenyl)-4-methyl-8-methoxy-4,5-dihydro-3H-2,3-benzodiazepine,
3-acetyl-1-(4-aminophenyl)-4-methyl-8-methoxy-3H-2,3-benzodiazepine,
3-n-propionyl-1-(4-aminophenyl)-4-methyl-8-methoxy-3H-2,3-benzodiazepine,
3-cyclopropylcarbonyl-1-(4-aminophenyl)-4-methyl-8-methoxy-3H-2,3-benzodiazepine
according to claim 1.

3. A compound of claim 1, wherein the optional substituents of $C_1$–$C_6$ alkyl or $C_6$–$C_{10}$ aryl are $C_1$–$C_6$ alkoxy or halogen.

4. A compound of claim 3 wherein $C_1$–$C_6$ is methyl, ethyl, propyl, isopropyl, butyl, isobutyl, sec-butyl, tert-butyl, pentyl, isopentyl or hexyl; halogen is fluorine, chlorine, bromine or iodine; $C_6$–$C_{10}$ aryl is naphthyl or phenyl; $C_3$–$C_7$ cycloalkyl is $C_3$–$C_5$ cycloalkyl; alkenyl is 1-propenyl, 2-propenyl, 3-methyl-2-propenyl, 1-butenyl, 2-butenyl, methallyl or vinyl; and alkanoyl is formyl, acetyl, propionyl, butanoyl, isopropylcarbonyl, caproyl, valeroyl or trimethylacetyl.

5. A compound of claim 3, wherein R² and/or R¹ is $NH_2$ or $NO_2$.

6. A compound of claim 3, wherein R² and/or R¹ is $NO_2$.

7. A compound of claim 3, wherein R² and/or R¹ is $NH_2$.

8. A compound of claim 3, in the form of a diastereomer.

9. A compound of claim 3, in the form of an enantiomer.

10. A compound of claim 3, in the form of a tautomer.

11. A compound of claim 3, in the form of an E or Z isomer.

12. A process for the production of a compound of formula I according to claim 1, comprising
a) cyclizing with $H_2N$—NH—R³, wherein R³ has the meaning as in claim 5, a compound of formula II

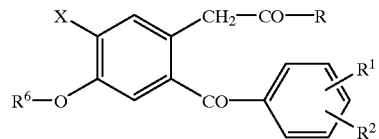

(II)

in which R¹, R², R⁶ and X have the meaning as in claim 5 and R is hydroxy or $C_{1-6}$ alkyl, or
b) reacting with $H_2N$—NHR³, wherein R³ has the meaning as above, a compound of formula III

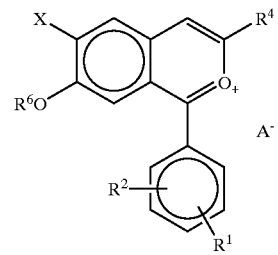

III in which R¹, R², R⁴, R⁶ and X have the above meaning and A⁻ means an anion of an inorganic base,
and optionally then reducing the nitro group and/or the 3,4-double bond and/or modifying the compound by reduction, dehalogenation, acylation, alkylation, hydroxylation, halogenation, or introduction of a carbamoyl group or an ester group, and
c) separating the isomers or forming salts of the compound made by method a) or b).

13. A pharmaceutical composition comprising a compound of formula I according to claim 3 and a pharmaceutically acceptable carrier.

14. A pharmaceutical composition of claim 13, which is the form of a tablet, suppository, capsule, solution, suspension, or emulsion.

15. A method of treating a disease associated with overstimulation of an AMPA receptor, or hyperactivity of an excitatory amino acid, comprising administering to a patient in need thereof an effective dose of a compound of claim 3.

16. The method of claim 15, wherein the disease is a neurologic or psychiatric disorder.

17. The method of claim 15, wherein the compound is administered enterally, parenterally or orally.

18. The method of claim 15, wherein the compound is administered in a daily dose of 0.5–1000 mg.

19. The method of claim 18, wherein the daily dose is 50–200 mg.

* * * * *